(12) United States Patent
Weischedel

(10) Patent No.: US 8,368,395 B2
(45) Date of Patent: Feb. 5, 2013

(54) MAGNETIC INSPECTION DEVICE AND METHOD FOR DETECTING LOSS IN METALLIC CROSS SECTION

(75) Inventor: Herbert R. Weischedel, South Windsor, CT (US)

(73) Assignee: NDT Technologies, Inc., South Windsor, CT (US)

( * ) Notice: Subject to any disclaimer, the term of this patent is extended or adjusted under 35 U.S.C. 154(b) by 523 days.

(21) Appl. No.: 12/336,585

(22) Filed: Dec. 17, 2008

(65) Prior Publication Data

US 2010/0148766 A1 Jun. 17, 2010

(51) Int. Cl.
*G01N 27/82* (2006.01)
(52) U.S. Cl. .......................... 324/238; 324/240; 324/251
(58) Field of Classification Search .................. None
See application file for complete search history.

(56) References Cited

U.S. PATENT DOCUMENTS

| | | | |
|---|---|---|---|
| 3,424,976 A | | 1/1969 | Jezewski et al. |
| 4,096,437 A | * | 6/1978 | Kitzinger et al. ............. 324/227 |
| 4,659,991 A | | 4/1987 | Weischedel |
| 5,751,144 A | * | 5/1998 | Weischedel .................... 324/240 |
| 5,804,964 A | * | 9/1998 | Hamelin et al. ............... 324/242 |
| 6,057,684 A | * | 5/2000 | Murakami et al. ............ 324/240 |
| 6,265,870 B1 | | 7/2001 | Weischedel |
| 2003/0011363 A1 | | 1/2003 | Wayman et al. |

FOREIGN PATENT DOCUMENTS

| | | |
|---|---|---|
| JP | 5164745 A | 6/1993 |
| JP | 7072122 A | 3/1995 |
| WO | 2008093410 A1 | 8/2008 |

OTHER PUBLICATIONS

International Search Report for Serial No. PCT/US2009/067970 dated Dec. 15, 2009.

* cited by examiner

*Primary Examiner* — Minh N Tang
(74) *Attorney, Agent, or Firm* — McCormick, Paulding & Huber LLP

(57) ABSTRACT

A magnetic inspection device for nondestructively inspecting elongated objects, such as wire cables, pipes, and the like, for loss of metallic cross-section due to abrasion, corrosion, and external and internal discontinuities, having a magnet for inducing in sections of the object between the stations, magnetic flux at the saturation level. A magnetic flux detector having magnetic sensors positioned between the poles and laterally of the elongated object utilizes shields and flux decompressors to render the flux detector more sensitive to leakage flux caused by discontinuities in the objects.

23 Claims, 6 Drawing Sheets

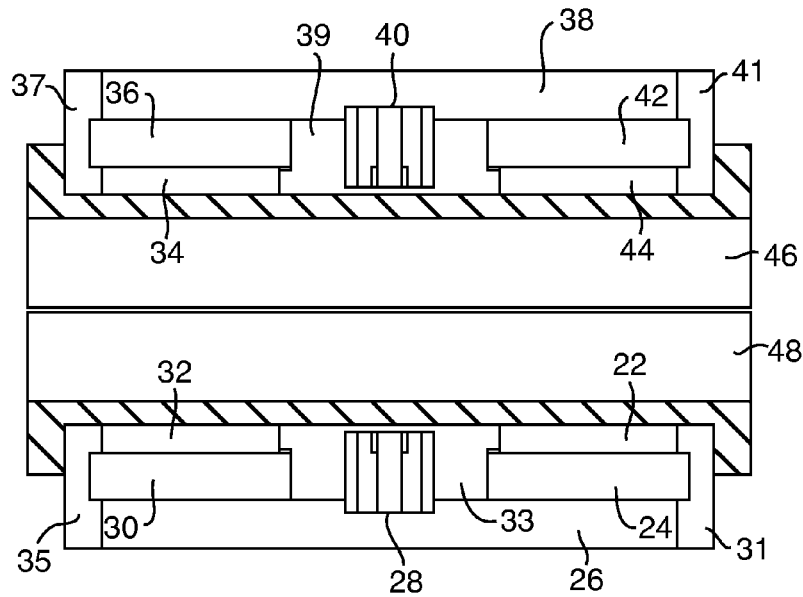

MAGNETIC INSPECTION DEVICE AND METHOD FOR DETECTING LOSS IN METALLIC CROSS SECTION

STATEMENT REGARDING FEDERALLY SPONSORED RESEARCH

This invention was made with government support under Contract Nos. N62473-07-C-4088 and N00244-07-C-0064 awarded by the Department of Navy. The government has certain rights in the invention.

FIELD OF THE INVENTION

The present invention relates to nondestructive magnetic inspection devices for evaluating elongated objects such as wire cables, rods, pipes, and the like, and is concerned more particularly with a magnetic testing method and device for detecting loss in metallic cross section in the objects due to distributed or localized discontinuities on the surface or within the object. The invention may be utilized both at the manufacturing level and/or in the field.

BACKGROUND OF THE INVENTION

Reliable and rational techniques for assessing the condition of wire cabling, rods, pipes, and similar elongated ferromagnetic objects such as visual and electromagnetic inspections are known in the art, but depend extensively on the experience and intuition of the human inspector. Serious accidents, various non-scheduled equipment downtimes, and premature replacement as precautionary measures are all consequences of the state of the art, quite apart from the costs involved in the inspection process. Accordingly, it is desirable to provide an improved technique for testing and measuring the actual strength and remaining life in the metallic objects.

One of the primary problems in prior art magnetic inspecting devices is the bulk and weight of most of the devices. Both of these factors limit the applications of the devices and reduce the resolution of the signals that are generated. Test signals are complex and are frequently accompanied by high levels of noise due to non-homogeneities and the coarse construction of objects under test. As a result, data interpretation often is a mixed product of both art and science.

The inspection process addresses two general types of discontinuities that are observed especially in wire cables. The first is a localized discontinuity, such as a broken wire within the cabling, and the second is a distributed discontinuity such as the loss of metallic cross section due to corrosion or abrasion. Both of these discontinuities cause a reduction in metallic cross section and, consequently, affect cable life and strength.

There are several methods of magnetically testing elongated objects such as cables for localized or distributed discontinuities. One of these methods is designated the main flux method and measures the amount of flux that can be carried by the cable between two longitudinally spaced stations. Since the total flux is directly related to the metallic cross sectional area of the object, measurements of the change in flux can be used to detect and measure the loss of area. U.S. Pat. No. 4,096,437 discloses a specific testing device of this type and includes Hall effect devices for measuring the amount of flux in the region of magnetic poles located at the spaced longitudinal stations along a cable. Changes in the cross sectional area caused by corrosion and abrasion can be measured in absolute terms, and relative movement of the cable with respect to the measuring device does not enter into the test parameters. One of the disadvantages, however, is that an extended section of the cable is inspected at any given moment. Therefore, only the average value of the metallic cross sectional area is measured with a considerable loss of resolution. Also, small flaws, such as those caused by broken wires or cluster of wires, and other localized discontinuities are difficult to detect.

Another method of testing employs a saturated magnetic field extending axially through a section of cabling under test and measures changes in leakage flux due to disruptions or breaks in the rope at the surface of the cable. Flux sensors, such as Hall Effect sensors or coils, may measure the changes as sensors and cable are moved relative to one another, and the test signals derived from the sensors may be displayed on a strip-chart recorder that is driven in synchronism with the relative movement of the sensor and cable. U.S. Pat. No. 3,424,976 and U.S. Pat. No. 4,096,437 discloses specific examples of leakage flux detectors.

The advantages of leakage flux systems are that small external and internal flaws, such as broken wires, can be detected and a qualitative indication of corrosion and abrasion is also available. The disadvantages of the prior art systems are that the reduction in cross-sectional area caused by abrasion and corrosion cannot be determined quantitatively, and since the measurements are representative of changes in the leakage flux, signal amplitudes for coils are proportional to the test speeds. As a result of the latter, tachometers are frequently used in connection with an automatic gain control circuit to equalize the signals for recording purposes. This adds complexity and weight to the instruments, and additionally, a certain minimum speed is generally required for a threshold signal. Because of the non-homogeneous structure of wire cabling, test signals are very noisy, and the noise signal cannot be removed by filtering because the differences in the levels of the noise and flaw signals are very small. Still further, because of the requirement for movement between the magnetic device and the cable, the process cannot be carried out at the ends of a cable, which is permanently secured in place.

One known method that is used to overcome the disadvantages listed above has magnets, which induce a saturated magnetic field axially through a short section of the cable as the device and the cable move relative to one another. A sensing coil located in close proximity to the cable between the magnetic field poles detects small changes in leakage flux at the surface of the cable in the saturated condition. The sensed flux changes are applied to an integrator to measure the net variation in flux and correspondingly the total change in cross section. Multiple sense coils mounted on core pieces conforming to the external surface of the cable ensure complete continuity of the inspection process and allow the magnetic device to be installed and removed at intermediate stations along the cable. U.S. Pat. No. 4,096,437 and U.S. Pat. No. 4,659,991 disclose a specific testing device of this type.

The disadvantage of a system using sensing coils is that the coil sensors require fairly elaborate electronic analog circuitry that cannot be accommodated on the sensor head. What is needed is an autonomous sensor head to perform all signal processing aboard the sensor head, or to eliminate supplementary analog circuitry altogether.

Other state of the art devices for nondestructive inspection of elongated magnetically permeable objects such as pipes can be found in U.S. Pat. No. 6,265,870 and U.S. Pat. No. 5,751,144. These devices use an eddy current sensor assembly to inspect elongated permeable objects. The sensor assembly has an auxiliary magnet including first and second auxiliary magnetic poles oppositely polarized relative to each other and spaced from one another for positioning and movement longitudinally relative to an elongated magnetically permeable object to be tested. The auxiliary magnet is interposed between primary magnets of the magnetic inspection device. A ferromagnetic member couples the first and second auxiliary magnetic poles. Compliant pole pieces such as magnetically permanent brushes are coupled to the auxiliary poles and are to be interposed between the auxiliary poles and the object to be inspected. An eddy current sensor is disposed between the auxiliary magnetic poles and includes a sensor body and a means coupled to the ferromagnetic member for urging the sensor body against an opposing surface of the magnetically permeable object to be inspected. The eddy current sensor is able to detect longitudinal discontinuities such as stress corrosion cracks and the like.

The problem with all of the patents listed above is that there is a strong presence of secondary flux between the magnetic poles that can affect the sensitivity of the magnetic flux detector and makes the accurate detection of loss of metallic cross section or localized discontinuities difficult.

Accordingly, it is a general object of the present invention to provide a method and apparatus for quantitatively determining the loss of metallic cross section caused by corrosion, abrasion and other factors, and to also obtain at least a qualitative measurement of localized discontinuities in elongated magnetically permeable objects without the disadvantages mentioned above.

SUMMARY OF THE INVENTION

One aspect of the present invention resides in a magnetic inspection device for nondestructively detecting structural faults and discontinuities in elongated magnetically permeable objects such as wire cables, rods, pipes, tank, walls, ship hulls, and the like. The magnetic inspection device has a magnet with two opposite magnetic poles spaced apart from one another at longitudinally spaced stations for positioning and movement relative to an elongated magnetically permeable object to be inspected. The magnet induces in the sections between the stations magnetic flux at the saturation level. The magnet also defines a ferromagnetic flux return path between the poles externally of the object for completing a flux circuit. The magnetic inspection device has a magnetic sensor assembly that has a magnetic flux detector. The magnetic flux detector is positioned between the poles and stations adjacent to the elongated object. The sensing portion of the magnetic flux detector faces the surface of the elongated object between the two poles of the magnet for sensing perturbations in leakage flux at the exterior surface caused by discontinuities in the object. The sensing of perturbations is done as the object and the inspection device move relative to one another. Further, the magnetic inspection device has a flux decompressor located between the magnetic poles of the magnet and adjacent the magnetic flux detector for reducing secondary flux at the surface of the object in the vicinity of the detector and allowing a more pronounced expression or drawing out of leakage flux at the surface of the object due to the fault or discontinuity.

Another aspect of the present invention has a flux shield in the vicinity of the magnetic flux detector. The flux shield is located between the magnetic sensor assembly and each pole of the magnet. The flux shields absorb secondary flux between the poles in the vicinity of the flux detector to aid the magnetic sensor assembly in sensing the perturbations of leakage flux.

Another aspect of the present invention resides in a method for nondestructively inspecting an elongated magnetically permeable object, such as wire cables, pipes, tank walls, well casings, ship hulls, and the like, for loss in metallic cross section, local external and internal discontinuities, abrasion, corrosion and the like. The method includes the step of inducing a magnetic field extending longitudinally through the elongated magnetically permeable object between longitudinally spaced stations at a saturation level. The field is part of the magnetic circuit through the object between the spaced stations. The circuit is closed externally of the object by a ferromagnetic flux return path or paths. A magnetic sensor assembly(s) with a magnetic detector(s) is provided to detect leakage flux from the object. The magnetic sensor assembly(s) is shielded from secondary flux passing between the poles to improve the leakage flux detection. The magnetic field and spaced stations are moved progressively and longitudinally along the object and sensing the changes in leakage flux at the exterior surface of the object due to changes in metallic cross section of the object.

Another aspect of the present invention resides in a method for nondestructively inspecting an elongated magnetically permeable object that includes a magnetic flux decompression step. A magnetic field is induced in the elongated magnetically permeable object between longitudinally spaced poles at the saturation level. A magnetic sensor assembly having a magnetic flux detector is provided to detect leakage flux at the surface of the object. The flux between the magnetic poles in the vicinity of the magnetic flux detector is decompressed in and around the object, while the magnetic field and spaced poles move progressively longitudinally along the object to allow a more pronounced expression of leakage flux at the exterior surface of the object due to changes in metallic cross section.

BRIEF DESCRIPTION OF THE DRAWINGS

FIG. 1 is a schematic illustration of a section of a magnetic inspection device in accordance with the present invention for detecting loss of metallic cross section in an elongated magnetically permeable object, such as a wire cable, pipe, or the like.

FIG. 4 schematically illustrates in longitudinal cross section a more detailed representation of the preferred embodiment of the magnetic inspection device in FIG. 3.

FIG. 5 is an enlarged schematic cross section of the sensor assembly of the magnetic device of FIG. 3.

FIG. 6 is a perspective view showing the sensor assembly in the preferred embodiment.

FIG. 7 is a schematic transverse cross sectional view of the magnetic inspection device surrounding an elongated object.

FIG. 11 is an enlarged schematic illustration of still another embodiment of the magnetic inspection device in the absence of a sensor assembly of the present invention shown inspecting the wall of a pipe or the like.

FIG. 12 is an enlarged schematic illustration of the embodiment of FIG. 11 with the sensor assembly of the present invention including a decompression bar and flux shields at a discontinuity in the wall of a pipe or the like.

FIG. 13 is a schematic illustration of a differential data acquisition system of the magnetic inspection device.

DETAILED DESCRIPTION OF EMBODIMENTS

Figure 1:
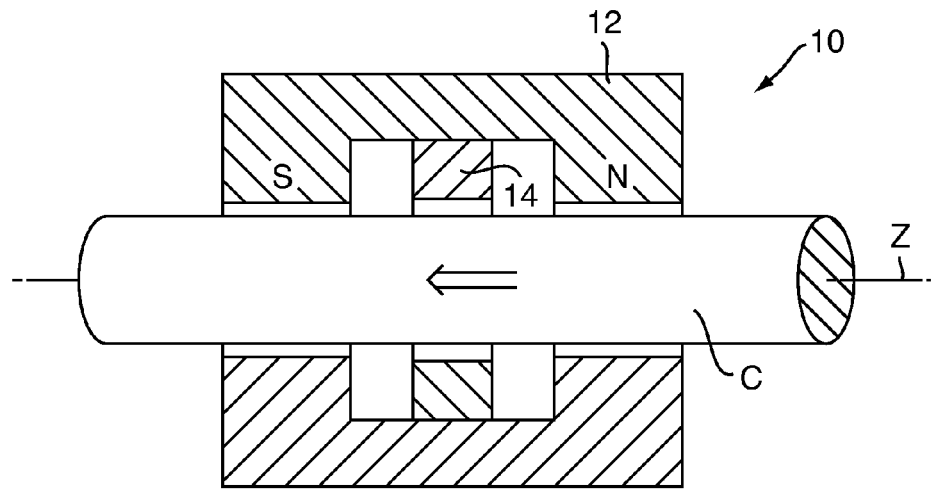

FIG. 1 illustrates a section of a magnetic inspection device 10 for nondestructively detecting loss of metallic cross section in elongated ferromagnetic objects such as but not limited to a wire cable C. Loss in metallic cross section can occur due to abrasion through use, corrosion, and also due to local discontinuities such as fractures or breakage of individual wires on the exterior surface of the cable C or internally. The magnetic device 10 may be used to inspect cables C or the like, either in the manufacturing process or in a working environment without removing the cable C from its normal operating position. The magnetic device 10 may also be used for inspecting other types of elongated, magnetically permeable objects, such as pipes, rods, bars, billets, storage tanks, hulls, and the like.

The magnetic device 10 is comprised of a permanent magnet or magnets 12 for inducing a saturated magnetic field axially through the cable C in the longitudinal direction. The permanent magnet(s) 12 has north and south poles located at spaced longitudinal stations along the cable C.

A sensor assembly 14 is located at a position midway between the poles of the magnet(s) 12 and lies in a plane perpendicular to the longitudinal axis Z of cable C. The sensor assembly 14 substantially circumscribes the entire circumference of the cable C in close proximity to the exterior surface and detects changes in leakage flux as the cable C and device 10 move relative to one another in the longitudinal direction. Relative movement may be produced in a variety of manners. In installations where the cable C is normally moved, such as cranes, elevators, mine hoists, and cable cars the device is normally mounted in a stationary position, and the cable C is pulled through the device. In other installations where the cable C is normally stationary, such as guy lines, suspension cables, and the like, the instrument may be pulled or driven along the cable C.

Figure 2:
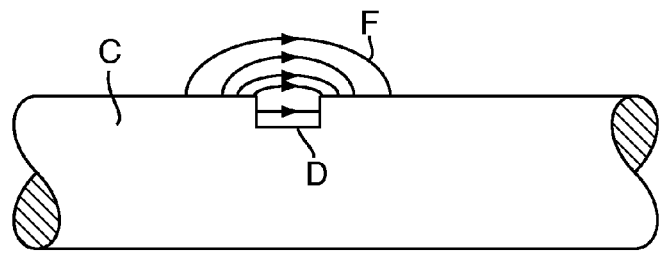
FIG. 2 is a schematic illustration of leakage flux that exists on the exterior surface of magnetically saturated wire cable in the vicinity of a defect in the cable.

FIG. 2 illustrates local perturbations in leakage flux F that are created where a reduction or loss in the metallic cross-section of the cable C exists. Since the magnetic device 10 induces a saturated field in the cable C, any reduction in cross section due to a defect D forces or expresses lines of flux out of the cable C and produces a local perturbation of flux F that can be detected by the sensor assembly 14 of FIG. 1 as the lines of flux pass through the sensor assembly. The radial location of the local discontinuity D, either at the core of the cable C or at its exterior surface produces the same effect, and only influences the strength of the signal that is sensed. The azimuthal location of the local discontinuity D also causes the leakage flux F to be expressed more prominently on one part of the exterior surface than another, and in order to ensure that all discontinuities are detected regardless of location, the sensor assembly 14 circumscribes substantially the full periphery of the cable C at the station intermediate the poles of the magnet 12. Gradual changes in the metallic cross section due to corrosion or abrasion also produce changes in the leakage flux F in essentially the same manner over a longer section of the cable C. Such changes also are detected through the sensor assembly 14 at a lower signal level due to a less rapid change in the leakage flux F pattern.

The apparatus illustrated in FIG. 1 has a single continuous sensor assembly 14 that substantially circumscribes the elongated magnetically permeable object such as a wire rope or cable C. Unfortunately in this configuration the apparatus of FIG. 1 cannot be mounted on or removed from a cable C except at the cable C ends. This is impractical in many situations, and consequently another embodiment of the invention is shown schematically in FIGS. 3 and 4.

Figure 3:
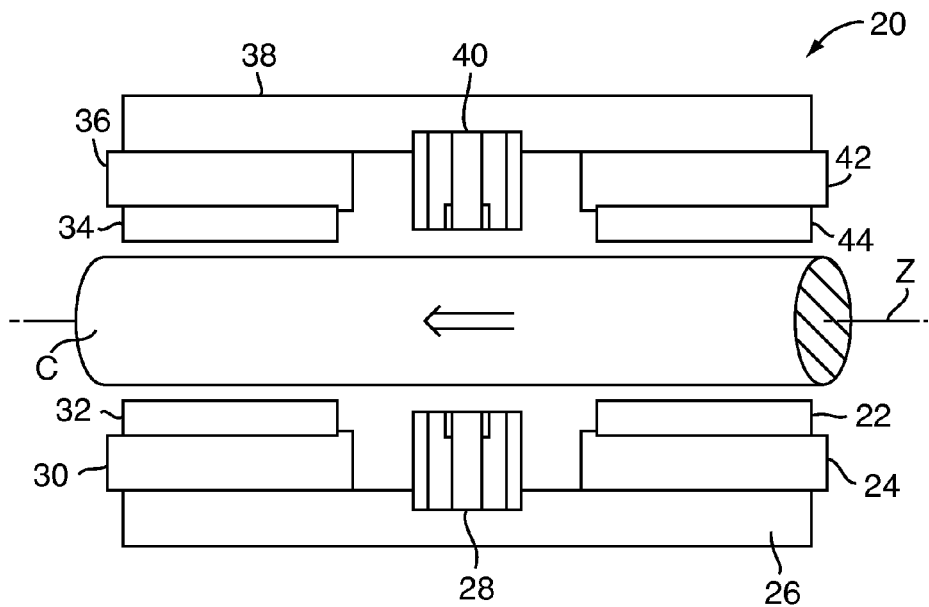
FIG. 3 schematically illustrates in longitudinal cross section a preferred embodiment of the magnetic inspection device in accordance with the present invention along a longitudinal section of a cable.

FIG. 3 shows a magnetic device 20 with a set of semicircular or segmented permanent magnets 24, 30 and poles 22, 32 disposed along one lateral side of the elongated cable C and another set of semicircular magnets 36, 42 and poles 34, 44 at the opposite side. The magnets 24, 30 are interconnected by a ferromagnetic bar or bars 26 to provide a magnetic flux return path or paths between the magnets 24, 30 for the magnetic flux that is induced in the cable C. In a similar manner, a ferromagnetic bar or bars 38 interconnect the permanent magnets 36, 42 on the other side. In this embodiment, the magnets themselves form the pole pieces to generate the flux in the cable C at the saturation level.

Two magnetic sensor assemblies 28, 40 are located generally in a transverse plane between the respective sets of magnetic poles. The sensor assemblies 28, 40 are located in close proximity to the exterior surface of the cable C for detecting perturbations in leakage flux F at the exterior surface of the cable C as explained above in connection with FIGS. 1 and 2.

FIG. 4 shows the magnetic inspection device 20 of FIG. 3 with cable guides 46, 48 and without the cable C. These guides 46, 48 are made of a non-magnetic material such as plastic and protect the sensor assemblies 28, 40 from grease and dirt that is commonly found on cables, guy wires, and the like. The sensor assemblies 28, 40 correspond to the sensor assembly 14 in FIG. 1 for detecting change in leakage flux at the exterior surface of cable C. The correspondence arises due to the fact that the sensor assemblies 28, 40 lie adjacent the exterior cable C surface in the same manner as the sensor assembly 14 (of FIG. 1) for detecting changes in leakage flux and the sensor assemblies 28 and 40 collectively circumscribe the cable C. Elements 31, 33, 35, 37, 39, and 41 are nonmagnetic support structures.

With the separate sensor assemblies 28, 40 in the magnetic device 20 can be manufactured with two separable housing portions for mounting and demounting the device on an elongated ferromagnetic object at any station intermediate its ends. It is not essential to have multiple poles and magnets as shown; however, the symmetric construction assures a uniform flux density in the field through the cable C and permits operation of the device 20 at the saturation level to be achieved with greater certainty. With particularly large cables, multiple sets of magnets are more manageable and preferable.

FIG. 5 schematically shows an enlarged cross section of the sensor assembly 28 with a set of complementary Hall sensors 56. The sensor assembly 28 includes a flux shield or shields 50, 58 on each side of the Hall sensors 56. The complementary Hall sensors 56 are mounted on a flux collector plate 54 which helps attract leakage flux from a defect in the object being inspected. The sensors are mounted on the end of the plate 54 which faces the object being inspected.

FIG. 6 shows in a perspective view one embodiment of the sensor assembly 28 and the actual placement of sets of the complementary Hall sensors on the flux collector plate between the shields. The complementary sets of hall sensors 52, 56 are spaced on the flux collector plate 54 with a sensor portion facing the inside of the arc closest to the cable C being inspected. The other sensor assembly 40 has a similar construction.

FIGS. 6 and 7 show possible locations of hall sensors in a sensor assembly 28. The plurality of complementary hall sensors are spaced from one another and disposed generally in a single plane about the exterior surface of the cable C being inspected. FIG. 7 shows four sets of the complementary hall sensors 52, 56, 60, 62 distributed at different portions of the exterior surface of the cable C. The importance of the flux shields and flux collector plate or plates will become more apparent in the discussion below and accompanying figures.

Figure 8:
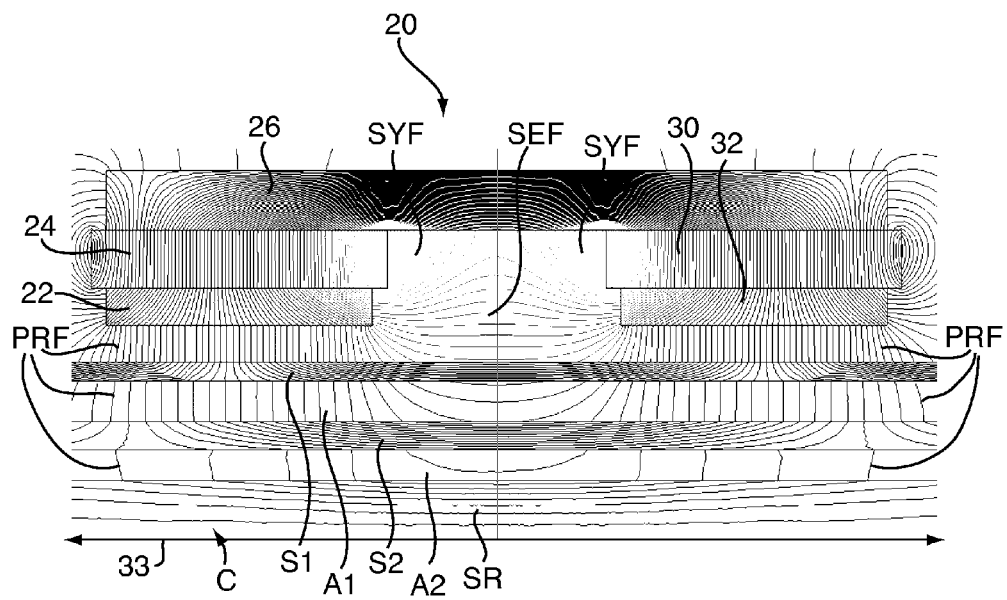
FIG. 8 is a schematic illustration of flux lines produced in and around an elongated object by the magnetic inspection device of FIG. 3 in absence of the sensor assembly of the present invention.

FIG. 8 is a 2-dimensional schematic illustration of the upper half of the inspection device 20 of FIG. 3, in the absence of the sensor assemblies of the present invention, and shows the flux lines of the magnetic field that are induced for inspection of a wire cable C. The portion of the cable C, above its centerline 35 is modeled in FIGS. 8-10 by two concentric steel tubes S1 and S2, and one solid steel rod SR made of cold rolled steel. Since wire cable C consists of a bundle of tube-like steel there can be air gaps A1, A2 in the cable C. The primary flux PRF can be seen flowing into the cable C starting with the steel tube S1, through the air space A1 into the steel tube S2 through the air space A2 and into the steel rod SR, so that the entire cable C is magnetically saturated.

The magnetic inspection device 20 is shown with the set of permanent magnets 24, 30 disposed about one lateral side of the cable C. The magnets are connected with ferromagnetic bar or bars or yoke(s) 26 to provide a magnetic flux return path(s) between the magnets 24, 30 for the primary flux PRF that is induced in and saturates the cable C. The primary flux PRF flows in the radial direction inside the inspection device 20 and leaves and enters the front surfaces of the pole pieces 22, 32 facing the cable at right angles. When a cable C is present, the primary magnetic flux PRF flows inside the cable C or object being inspected and is directly affected by any discontinuity or by a change in cross section in the object under inspection. Note that stray flux SYF leaves the permanent magnets 24, 30 and then returns to the yoke 26 and is not utilized for defect detection. The secondary flux SEF leaves and enters the side surfaces of the pole pieces 22, 32 and flows between the poles of the magnets 22, 32, mostly in the axial direction without entering the cable C. The secondary flux SEF is approximately constant and almost independent of the sensor assembly operating conditions, such as different metallic cross sections of the cable C under test. As a corollary of the above, the secondary flux SEF is only marginally affected by the primary flux PRF and has limited usefulness for assessing the condition of cables C or the like. The secondary flux SEF flowing in the inspection device 20 compresses or forces the primary flux PRF to stay in the cable C and causes the cable C to be magnetically super saturated (at a value above 2.0 Tesla).

Figure 9:
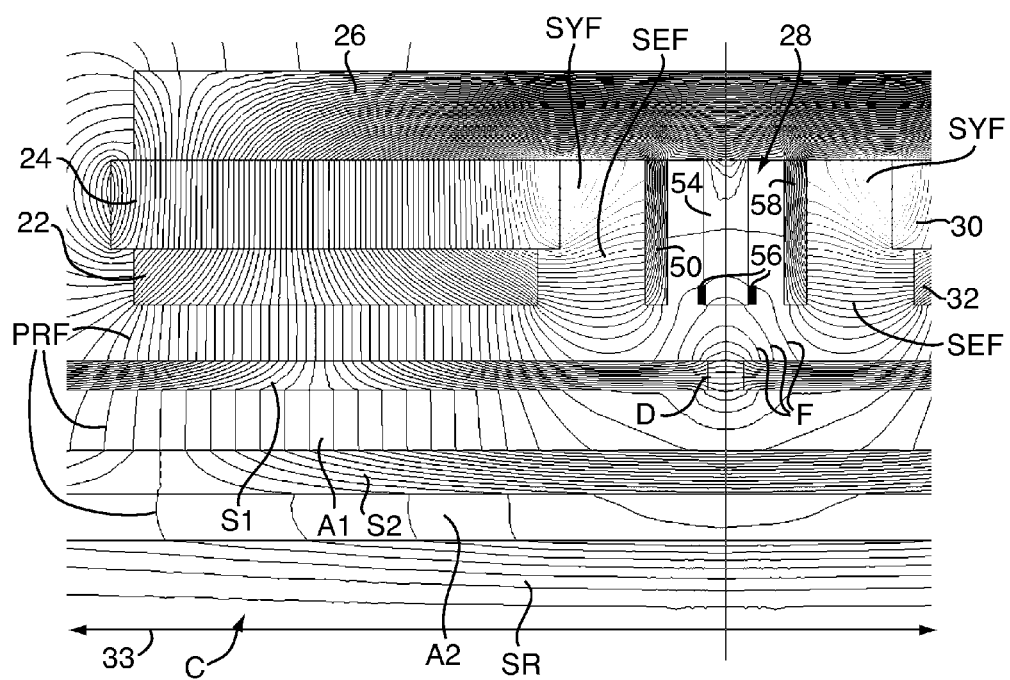
FIG. 9 is a schematic illustration of the magnetic inspection device of FIG. 8 with the sensor assembly of the present invention installed.

FIG. 9 is the magnetic inspection device of FIG. 8 inspecting a cable C having a discontinuity D. It can be seen that leakage flux F is present in the area of the discontinuity D. The leakage flux F is the part of the primary flux PRF that is expressed from the cable C by the discontinuity. Changes in the leakage flux are therefore representative of changes in cross sectional area of the cable C due to discontinuities and are measured by the sensor assembly 28. It can be seen in FIG. 9 that the ideal placement of hall sensors 56 to measure the leakage flux F would be as close to the cable C as possible. But cables C are not uniform and can contain contaminants such as dirt and grease so the hall sensors have to be spaced from the cable C and may not be close enough to the cable C to get an accurate measurement of the leakage flux F because the hall sensors would be located in the area where the secondary flux SEF is dominant.

The above-described problem is caused by the limited operating range (sensitivity) of hall sensors. The present invention solves this problem in several ways, such as the use of flux shields, flux collector plates, and decompression bars as discussed below.

To understand the present invention, the properties of magnetic flux lines as shown in FIGS. 2 and 8-12, must be understood. Magnetic flux lines tend to repel each other. In the absence of magnetic saturation, flux lines always leave and enter surfaces of ferromagnetic objects at right angles. It is well known in the art that ferromagnetic materials will saturate at flux levels of approximately 2T (Tesla). Thus, below the saturation level, a ferromagnetic material will substantially contain the flux lines passing through it. As saturation is approached, the flux lines may travel as readily through air as they do through a magnetic material. The property of a magnetic flux field that can be verified with field lines is that the magnetic field always makes complete loops. Magnetic field lines neither start nor end, although they can extend to and from infinity.

As can be seen in FIG. 9, the secondary flux SEF constrains the Primary flux PRF to the cable interior. In other words, the secondary flux SEF compresses the primary flux PRF keeping it in the cable C and drives the cable C beyond the steel saturation point (at about 2.1T). This situation is easy to visualize considering that flux lines repel each other. The secondary flux SEF, in turn, is constrained by the stray flux SYF.

FIG. 9 illustrates one method of solving the above mentioned problems of measuring leakage flux F in an elongated ferromagnetic object such as a cable C with hall sensors. FIG. 9 shows the magnetic inspection device of FIG. 8 with flux shields 50, 58 and a flux collector plate 54 added. The flux shields 50, 58 are made from a ferromagnetic material such as cold rolled steel, and are placed on each side of the sensor assembly (see FIGS. 5 and 6) between the assembly and the pole pieces 22, 32. As shown in FIG. 9, the flux shields 50, 58 attract and capture the secondary flux from the pole pieces and return it to the yoke or yokes 26 before the flux reaches the sensor assembly 28. The capturing of the secondary flux SEF also results in a decompression and expression or drawing out of the leakage flux F in the region of the sensor assembly between the shields 50, 58 for more precise detection and measurement of the discontinuities D.

In other words, the flux shields 50, 58 capture the secondary flux SEF, which in turn, decompresses the primary flux PRF inside the cable C in such a fashion that part of it leaks into the air space surrounding the cable C in the region of the sensor assembly 28 between the flux shields 50, 58. Within the sensor assembly, the primary flux PRF is then measured by the hall sensors 56 as an indicator of the cable C condition. In the decompression area between the flux shields 50, 58, the cable C is still magnetically saturated at a flux density of about 2T.

The leakage flux F between the flux shields 50, 58 is greater in the presence of the discontinuity D and can easily be measured by a Hall sensor. Part of the flux shields 50, 58 are also in magnetic saturation around 1.95T. Since the shields are magnetically saturated they can only divert a predetermined amount of magnetic flux to the yoke 26 depending on their thickness. Therefore, by changing the thickness of the flux shields 50, 58, the shields can be tailored to reduce the secondary flux SEF including part of the stray flux SYF between the flux shields 50, 58 adjacent to the area that is magnetically compressed. Similarly, the distance between the pole pieces can be designed and tailored to produce the desired amount of secondary flux SEF in the air space next to the area between the flux shields 50, 58 that is magnetically decompressed. A slight overhang of the permanent magnets 24, 30 beyond the edge of the pole pieces 22, 32 helps in better aligning the secondary flux SEF in the axial direction.

Also shown in FIG. 9 is a flux collector plate 54 that supports the hall sensors 56 between the flux shields 50, 58. The purpose of the flux collector plate 54 is to attract additional leakage flux F so that the hall sensors 56 can measure the flux more accurately. Further, the flux collector plate 54 provides an ideal mounting surface for the complementary hall sensors 56 at a projecting edge close to the exterior surface of the cable.

Figure 10:
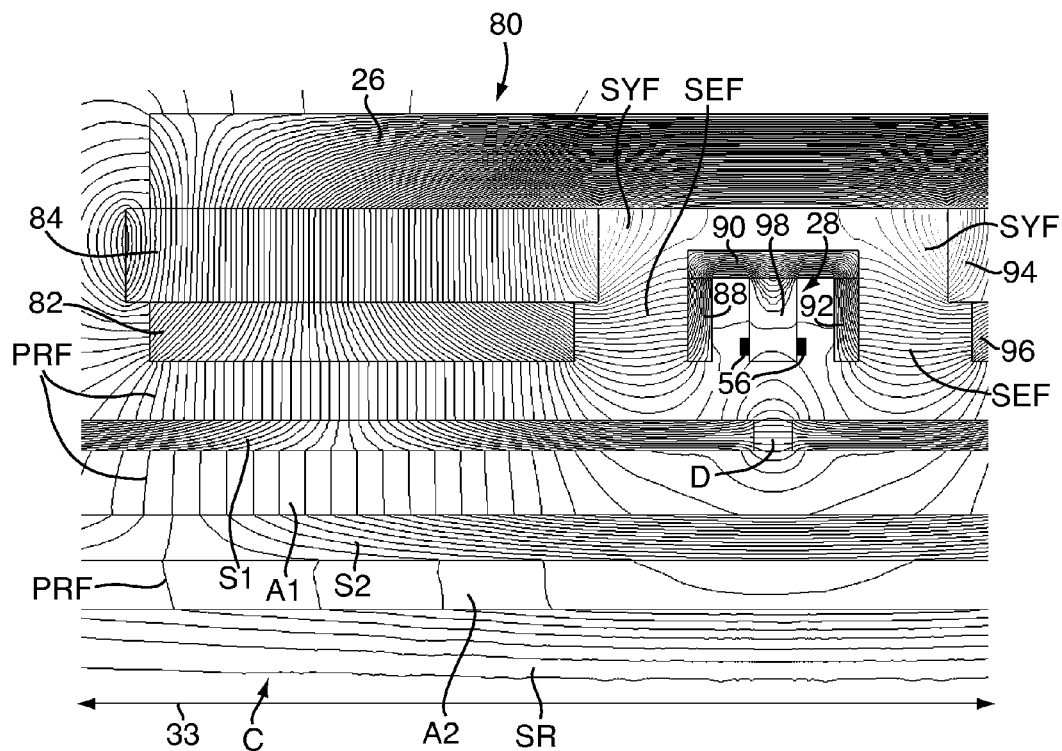
FIG. 10 is a schematic illustration of another embodiment of the present invention with a decompression bar or bars and flux shields for bypassing the secondary flux.

FIG. 10 illustrates an alternative embodiment of the present invention whereby the secondary flux SEF is bypassed from pole 82 to pole 96 instead of being returned to the yolk 26 as in FIG. 9. In this configuration the flux shields 88, 92 are connected to a decompression bar or bars 90 which pass the secondary flux SEF from shield 88 to shield 92 so that it bypasses the space in between the flux shields 88, 92 where the hall sensors 56 are located. Further, in this configuration the decompression bar 90 and flux shields 88, 92 decompress the primary flux PRF in the cable C in between the flux shields 88, 92 and allow leakage flux to be expressed into the sensor assembly 28. The thickness of the shields 88, 92 and of the decompression bar 90 controls the magnetic saturation level in each component. Therefore, by properly adjusting the thickness of these components, it is possible to optimize the design of a sensor assembly in such a fashion that, essentially, the entire secondary flux SEF is diverted away from the area between the sensor assembly and the cable C. This ensures that the hall sensors 56 will sense the leakage flux F exclusively. FIG. 10 shows, as in other embodiments, that a flux collector plate 98 can be added in between the flux shields 88, 92 as an extension of or attached to the decompression bar 90. The plate helps collect or attract the leakage flux F into the area between the flux shields 88, 92, to more accurately detect the leakage flux F and discontinuities D in the cable.

Figure 11:
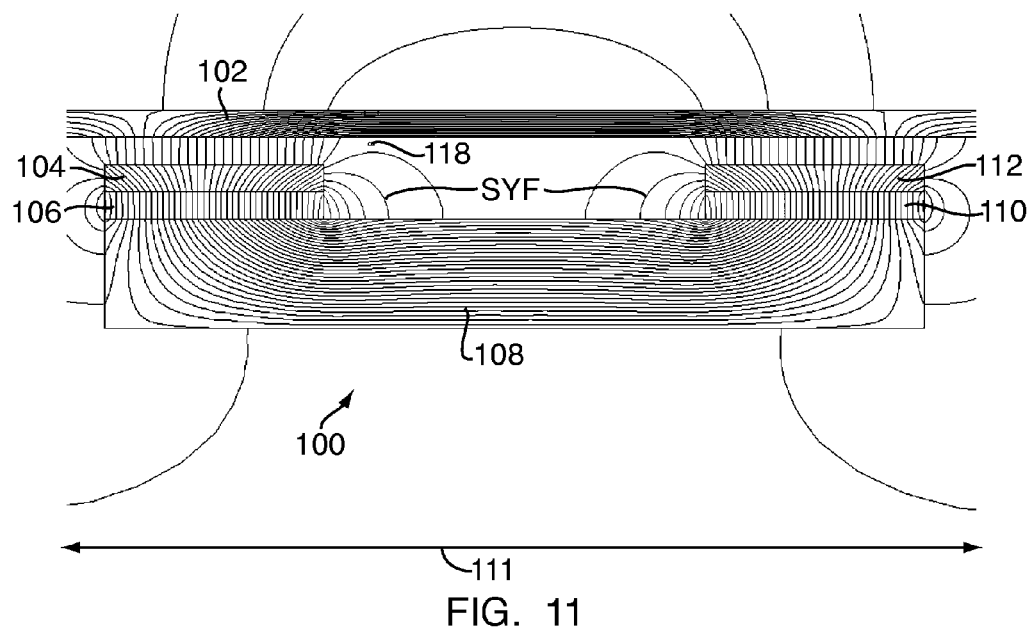

FIG. 11 is a schematic illustration of a device 100 without the present invention for inspecting a wall 102 of a pipe, storage tank, well casing, or the like. In this illustration the magnetic inspection device 100 is shown inside a pipe for inspection of the pipe wall 102. FIG. 11 is a cross sectional view of the rotationally symmetric device 100 known as a "pig" above the centerline or axis 111. The magnetic inspection device 100 has a yoke or yokes 108 that provide magnetic flux return path or paths for the permanent magnets 106, 110 and poles 104, 112. In this embodiment, ferromagnetic brushes or the like as shown in U.S. Pat. No. 6,265,870 can be attached to the pole pieces to contact the pipe wall 102 to avoid bouncing of the magnets 106, 110 over welds in the pipe wall. The magnets 106, 110 induce a magnetic flux in the pipe wall 102 so that the pipe wall 102 is magnetically saturated between the poles 104, 112. The magnetic inspection device 100 has Hall sensor(s) 118 schematically illustrated, between the poles 104, 112, but closer to the pole that is trailing in the direction of travel of the magnetic inspection device 100. In the present illustrated embodiment this would be pole 104. The sensor assembly of the present invention is not shown in this figure, in order to illustrate the lines of flux in the absence of the invention. No flux decompression occurs and the secondary flux or stray flux SYF is free to interfere with the detections of leakage flux by the sensor 118.

Figure 12:
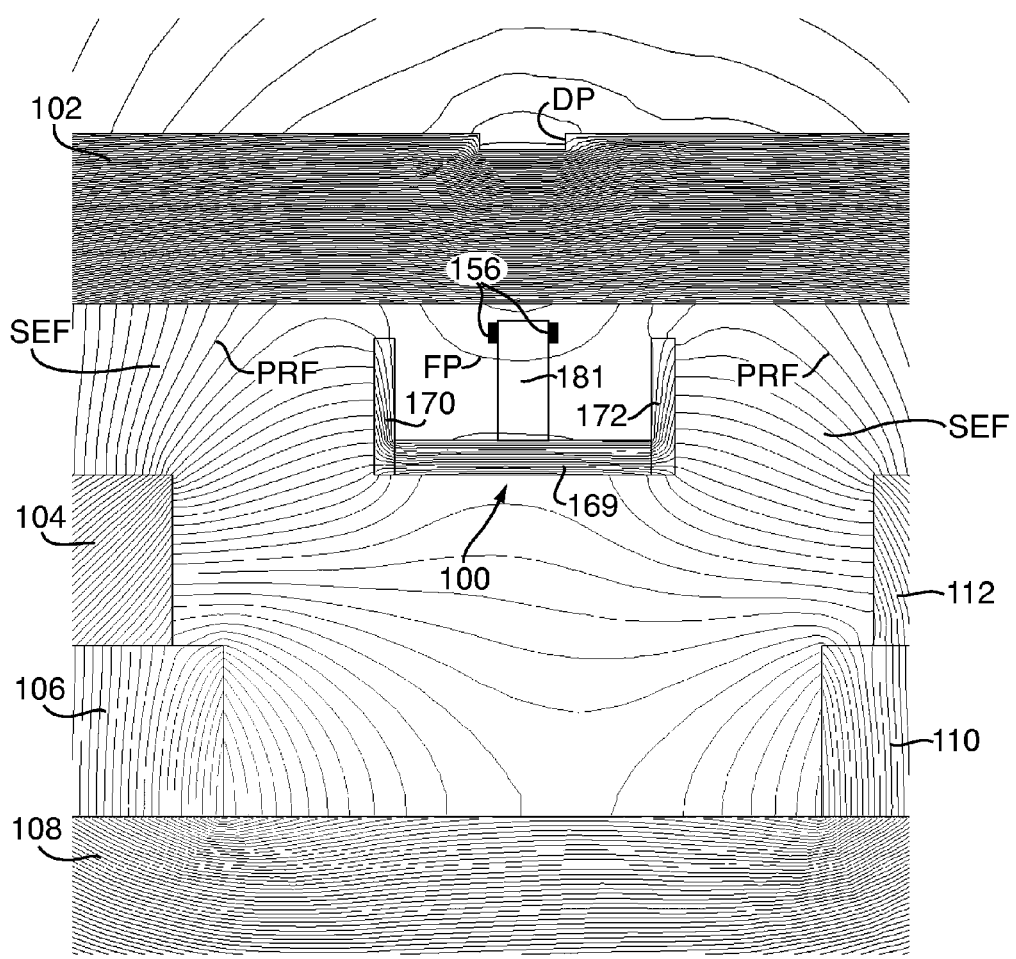

FIG. 12 is an enlarged view of the area of the magnetic inspection device 100 incorporating the features of the present invention for detection of the discontinuities DP in the pipe wall. A decompression bar 169 and flux shields 170, 172 have been added to each end of the decompression bar to aid in the bypassing of secondary flux SEF and decompression of the primary flux PRF in the vicinity of the hall sensor(s) 156. It can be seen that the leakage flux FP increases around the discontinuity DP for detection by the sensor(s) located between the flux shields 170, 172. Further, the flux collector plate or plates 181, located between the flux shields 170, 172 aid in attracting the leakage flux FP. The use of the flux shield(s), decompression bar(s), and flux collector plate(s) can be combined in different configuration best suited for the application of the magnetic inspection device. It can be seen that the secondary flux SEF compresses the primary flux PRF immediately before and after the sensor assembly 100.

FIG. 13 shows a schematic illustration of a differential data acquisition channel 67 for the hall sensors of the present invention. When measuring the low level signal produced by the leakage flux in the hall sensor 56, especially in an environment with high electromagnetic interference (EMI), noise can be a significant part of the signal. For such applications, double-ended or differential data acquisition should be used in order to eliminate common-mode voltage electromagnetic interference. This requirement is especially true where minute signals in the millivolt range with a rather large DC offset voltage must be accurately measured.

To implement a differential (or double ended) signal acquisition channel 67 for each set of hall sensors, a complementary or back-to-back arrangement is used. In FIG. 13, the complementary hall sensors 56a and 56b provide a voltage output that is proportional to the applied magnetic field. For example, the hall sensors 56a, 56b may have a quiescent output voltage that is 50% of the supply voltage V+ (typically 5V). The output Voltages $V_1$ and $V_2$ of hall sensors 56a and 56b are, respectively, $V_1 = V^+/2 + V_\Phi$, and $V_2 = V^+/2 - V_\Phi$, where $V_\Phi$ is the component of the hall sensor voltage that is induced by the applied magnetic field $\Phi$. The sensor output voltage $V_1$ and $V_2$ are fed respectively to the positive input 63 and negative input 65 of differential amplifier 68. The output voltage $V_c$, of the differential amplifier 68 therefore is $V_o = V_1 - V_2 = (V^+/2 + V_\Phi) - (V^+/2 - V_\Phi) = 2 V_\Phi$.

The simple rationale behind the differential measurement method is the fact that the complementary hall sensors 56a and 56b as well as other system components, such as wiring for each of the hall sensors, are essentially identical and located in close proximity to each other. Therefore, outside electromagnetic interference, if any, will induce substantially identical voltage noise components in the two branches of the differential circuit. As the mathematics above indicates, the outside electromagnetic interference or other noise is cancelled and the output voltage $V_O$ represents in purer form the voltage induced by the magnetic field $\Phi$ with multiplied gain.

Figure 14:
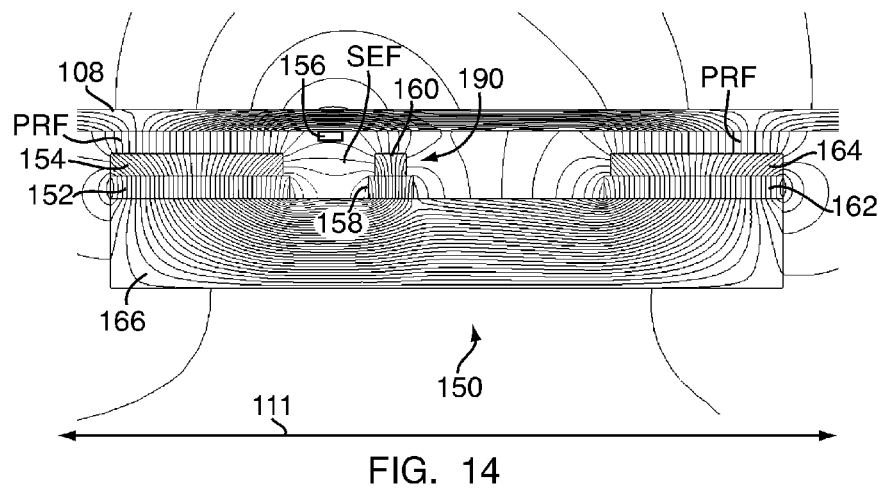
FIG. 14 is a schematic illustration of an alternative embodiment of the magnetic inspection device of FIG. 11 with an auxiliary permanent magnet and pole for inducing eddy currents in a pipe wall.

FIG. 14 shows an alternate embodiment of the magnetic inspection device which, for an inspection tool moving inside a pipe at a certain speed, produces a time-varying magnetic field in the wall of pipe 102 using an auxiliary magnet assembly or assemblies 190 consisting of a magnet(s) 158 and a pole or poles 160. The time-varying field produces eddy currents, as described in U.S. Pat. No. 5,751,144 and the changes in eddy currents representative of structural faults can be readily detected. The auxiliary magnet assembly 190 is located between the first and second primary magnets 152, 162 and associated poles 154, 164, and can include a housing (not shown) for supporting Hall sensor(s) 156 for eddy current detection. The auxiliary magnet 158 and pole 160 have the same magnetic poling as the primary magnet 162 and pole 164 and are positioned in the magnetic inspection device 150 between the primary poles 154 and 164.

The auxiliary magnet assembly 190 is located far enough downstream from the leading pole 164 so that the eddy currents produced from the leading pole 164 have decayed to zero and the pipe wall 102 is in a magnetically saturated state. The auxiliary magnet assembly 190 then regenerates supplemental eddy currents over the magnetically saturated portion of the pipe wall 102. The sensor(s) 156 is positioned downstream from the auxiliary pole 160 and adjacent to a portion of the pipe wall 102, where magnetic flux is in magnetic saturation and where the supplemental eddy currents have not decayed. When the eddy currents, which are circumaxial currents, cross a longitudinal stress corrosion fracture, or the like, the currents are interrupted and cause a change in the associated magnetic flux that can be detected by the invention. Since the magnetic flux of the previous embodiments flows primarily longitudinally and is not sensitive to a longitudinal discontinuity or stress fracture, detection of the eddy current generated flux constitutes an improvement in detecting the longitudinal stress fracture.

In the embodiment of FIG. 14, the secondary flux SEF is about constant and is not significantly affected by changes in the eddy currents. In order to remove the secondary flux and allow more sensitivity to the eddy current changes, a decompression bar(s) 169 is to bypass the secondary flux SEF in the vicinity of a sensor(s) 156 as shown in FIG. 15.

Figure 15:
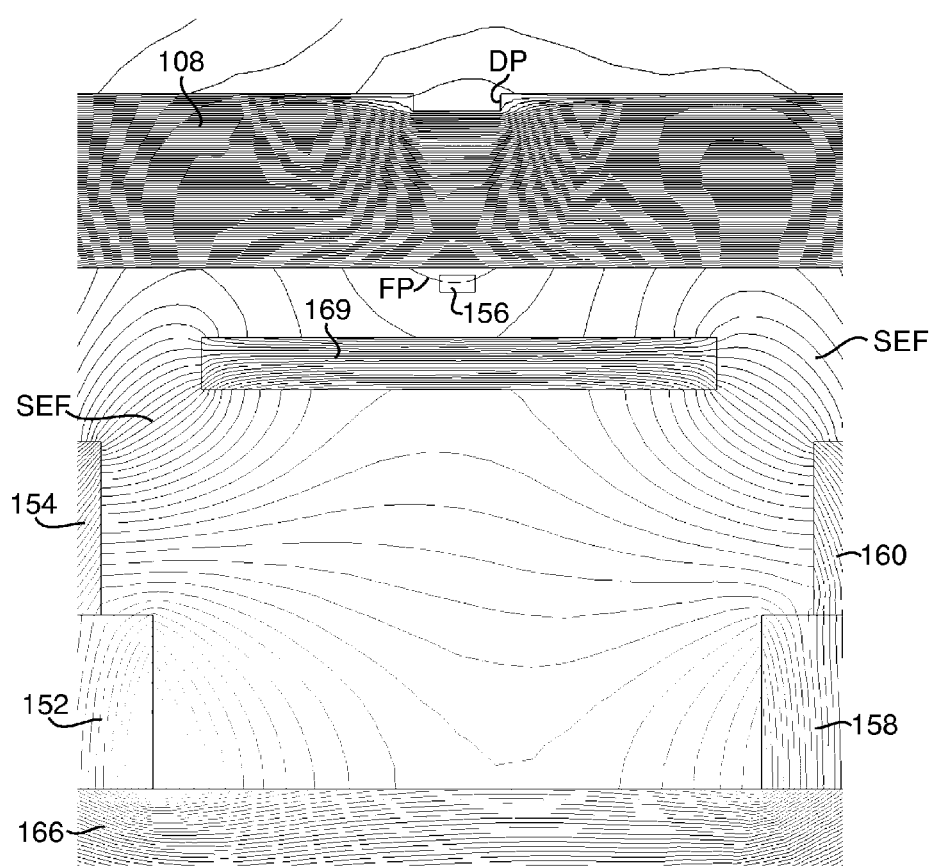
FIG. 15 is an enlarged schematic illustration of the embodiment of FIG. 14 further including a decompression bar, a discontinuity in the pipe wall, and associated lines of flux.

FIG. 15 is an enlarged view of the embodiment of FIG. 14 to show decompression bar or bars 169 in between the primary pole(s) 154 and the auxiliary pole(s) 160 and adjacent to the sensor(s) 156. The decompression bar 169 captures the secondary flux SEF and causes the flux to bypass the area in the vicinity of the sensor(s) 156, between the decompression bar 169 and the pipe wall 102. By bypassing the secondary flux SEF, flux in the pipe wall 102 in the area of the sensor(s) 156 is decompressed which allows minute changes in the leakage flux/eddy currents FP caused by discontinuities DP to be detected by the sensor(s) 156.

While the invention had been described with reference to the preferred embodiment, it will be understood by those skilled in the art that various obvious changes may be made, and equivalents may be substituted for elements thereof, without departing from the essential scope of the present invention. Therefore, it is intended that the invention not be limited to the particular embodiments disclosed, but that the invention includes all embodiments falling within the scope of the appended claims.

What is claimed is:

1. A magnetic inspection device for nondestructively detecting discontinuities in the form of loss in metallic cross section and localized discontinuities in elongated magnetically permeable objects, comprising:
    a magnet having two opposite magnetic poles and for inducing, in sections of a magnetically permeable object between the poles, a magnetic flux at the saturation level;
    a magnetic sensor assembly configured to substantially circumscribe the entire circumference of the object, the magnetic sensor assembly having a magnetic flux detector positioned between the poles for sensing perturbations in leakage flux at the exterior surface of the object and measuring changes in cross sectional area of the object, as the object and inspection device move relative to one another; and
    a flux shield located between the magnetic sensor assembly and each magnetic pole of the magnet for absorbing secondary flux between the poles and in the vicinity of the flux detector to aid the magnetic sensor assembly in sensing the perturbations of leakage flux.

2. A magnetic inspection device for detecting discontinuities as defined in claim 1, wherein one magnetic sensing element in the magnetic sensor assembly is a Hall sensor located between a pair of flux shields.

3. A magnetic inspection device for detecting discontinuities as defined in claim 1, wherein the magnetic sensor assembly includes: a pair of flux collector plates that substantially circumscribe the entire circumference of the object and a magnetic sensor mounted on each of the pair of flux collector plates for collecting leakage flux.

4. A magnetic inspection device for detecting discontinuities as defined in claim 3 wherein the magnetic sensor assembly includes: a pair of Hall sensors mounted spaced apart on the flux collector plate adjacent to the exterior of the object surface.

5. A magnetic inspection device for detecting discontinuities as defined in claim 3 wherein the flux shield and flux collector plate are made from cold rolled steel.

6. A magnetic inspection device for detecting discontinuities as defined in claim 1 wherein:
    a portion of the magnetic sensor assembly confronts the object and is shaped to conform to the exterior surface of the object; and
    a sensing portion of the magnetic sensor assembly is mounted adjacent to the confronting portion.

7. A magnetic inspection device for detecting discontinuities in elongated objects as defined in claim 1 wherein:
    the magnet has at least two sets of opposite magnetic poles for inducing magnetic flux simultaneously in the same section of the elongated object, one set of opposite magnetic poles being located adjacent one portion of the exterior surface of the object, and the other set of opposite magnetic poles being located adjacent another portion of the exterior surface of the object, each set of poles having separate flux return paths associated respectively with the sets of opposite magnetic poles, and
    the magnetic sensor assembly has two magnetic flux detectors and associated shield positioned respectively between the opposite magnetic poles for sensing perturbations of leakage flux at the respective exterior surface portions of the object.

8. A magnetic inspection device for detecting discontinuities as in claim 7, further including:
    a housing defining a central passageway through which an elongated object moves longitudinally of itself during inspection, and having two separable housing portions defined by a parting plane intersecting the central passageway along its length to permit the housing portions to be mounted in mating relationship over and removed from the elongated object intermediate the ends of the object; and
    one of the two magnetic flux detectors is supported in one of the separable housing portions and the other of the two magnetic flux detectors is supported in the other of the separable housing portions.

9. A magnetic inspection device for detecting discontinuities as defined in claim 8, wherein the separable housing portions are connected together by a hinge.

10. A magnetic inspection device for detecting discontinuities as defined in claim 8 wherein: the magnetic sensor assembly has a generally planar configuration and is divided into two halves, half being mounted in a respective one of the separable housing portions to mate with the other and circumscribe the central passageway and elongated objects therein when the separable housing portions are mounted over the object in mating relationship.

11. A magnetic inspection device for inspecting elongated magnetically permeable objects for abrasion, corrosion, and internal discontinuities, comprising:
a magnet having two magnetically opposite poles and a connecting ferromagnetic flux return path for movement relative to an elongated magnetically permeable object to be inspected, with the poles longitudinally separated along the object for inducing a saturated magnetic field in the portion of the object between the poles,
whereby changes in transverse cross section and internal discontinuities of the object produce detectable changes in leakage flux from the field between the poles at the exterior surface of the object;
a magnetic sensor assembly configured to substantially circumscribe the entire circumference of the object, the magnetic sensor assembly including a magnetic flux detector disposed between the longitudinally separated poles at one lateral side of an elongated object being inspected adjacent the exterior surface of the object with flux shields interposed between the longitudinally separated poles and the magnetic flux detector and a sensing portion of the detector exposed to the exterior surface of the object to detect the changes in leakage flux at the exterior surface of the object and measure changes in cross sectional area of the object as the object and magnetic inspection device move relative to one another.

12. A magnetic inspection device as defined in claim 11, wherein the sensing portion the magnetic flux detector includes a Hall sensor.

13. A magnetic device for inspecting elongated magnetically permeable objects as defined in claim 11, wherein: the magnetic flux detector has a generally planar configuration and is located in a plane perpendicular to the elongated object intermediate the two magnetic poles.

14. A magnetic device for inspecting elongated magnetically permeable objects as defined in claim 11 wherein: the magnetic flux detector is mounted between the flux shield at one side of the elongated object, and partially circumscribes the object with sensing portion in close proximity to the exterior surface of the object to intercept leakage flux at the surface.

15. A magnetic device for inspecting as defined in claim 11 wherein the magnetic flux detector comprises
a flux collector plate that has a generally arcuate configuration at one side to conform to generally cylindrical elongated objects;
the sensing portion includes a complementary set of Hall sensors mounted at the one side of the flux plate; and
the flux shields also comprise plates having arcuate configurations conforming generally to cylindrical elongated objects.

16. A magnetic device for inspecting elongated magnetically permeable objects, as in claim 11, wherein:
a plurality of the magnets having magnetically opposite, longitudinally separated poles and connecting flux return paths are disposed about a central passageway for an elongated magnetically permeable object and jointly movable relative to the object;
the magnetic flux detector includes a plurality of Hall sensors spaced from one another and disposed generally in a single plane about the exterior surface of the object between the shields.

17. A magnetic device for inspecting elongated magnetically permeable objects as defined in claim 15 wherein: the plurality of Hall sensors are mounted on flux plates and the flux plates collectively circumscribe the entire exterior surface of the object in said single plane.

18. A magnetic device for inspecting as in claim 15 further including:
a split housing having two separable portions defining a central passageway for the elongated object along a parting plane between the separable portions; and wherein:
two magnetically opposite poles of one magnet of the plurality and a Hall sensor is/are mounted in one of the separable housing portions; and another two magnetically opposite poles of another magnet of the plurality and a Hall sensor is/are mounted in the other of the separable housing portions.

19. A method for nondestructively inspecting an elongated magnetically permeable object for loss in metallic cross section, local discontinuities, abrasion, corrosion, internal discontinuities, comprising the steps of:
inducing a magnetic field extending longitudinally through the elongated magnetically permeable object between two longitudinally spaced magnetic poles at a saturation level, the field being part of a magnetic circuit through the object between the spaced magnetic poles, the circuit being closed externally of the object by a ferromagnetic flux return path;
providing a magnetic sensor assembly configured to substantially circumscribe the entire circumference of the object, the magnetic sensor assembly having a magnetic flux detector positioned between the magnetic poles to detect leakage flux from the object and measure changes in cross sectional area of the object;
shielding the magnetic sensor assembly between the magnetic poles from secondary flux passing directly between the magnetic poles; and
moving the magnetic field and spaced stations progressively and longitudinally along the object.

20. The method of claim 19 further including the steps of: bypassing the secondary flux between the magnetic poles in the vicinity of the magnetic flux detector.

21. The method of claim 19 further including: the step of sensing includes collecting leakage flux from the elongated magnetically permeable object.

22. The method of claim 21 wherein: the collecting of leakage flux is done with a flux collector plate.

23. A method of inspecting elongated magnetically permeable objects as defined in claim 19, wherein:
the step of inducing includes inducing a plurality of magnetic fields through a plurality of circuit portions to reach magnetic saturation in the object; and
the step of sensing further comprises employing a plurality of magnetic sensor assemblies circumscribing the object so that changes in magnetic flux around the full periphery of the object are sensed.

* * * * *